United States Patent [19]
Budmiger

[11] 4,155,122
[45] May 22, 1979

[54] LIGHT SHIELD FOR WELDER'S MASK

[75] Inventor: Hermann Budmiger, Seewen, Switzerland

[73] Assignee: Revue Thommen AG, Waldenburg, Switzerland

[21] Appl. No.: 856,178

[22] Filed: Nov. 30, 1977

Related U.S. Application Data

[63] Continuation-in-part of Ser. No. 637,000, Dec. 2, 1975, Pat. No. 4,071,912.

[51] Int. Cl.² .............................................. A61F 9/06
[52] U.S. Cl. ............................................ 2/8; 350/150
[58] Field of Search .......................... 2/8, 431, 432, 2; 350/150; 219/147

[56] References Cited

U.S. PATENT DOCUMENTS

| | | | |
|---|---|---|---|
| 2,773,422 | 12/1956 | Flynn, Sr. et al. | 2/432 X |
| 3,756,692 | 9/1973 | Scott | 2/431 X |
| 3,873,804 | 3/1975 | Gordon | 2/8 X |
| 3,943,573 | 3/1976 | Budmiger | 2/432 X |
| 4,039,254 | 8/1977 | Harsch | 2/8 X |
| 4,039,803 | 8/1977 | Harsch | 2/8 |

*Primary Examiner*—Peter Nerbun
*Attorney, Agent, or Firm*—Karl F. Ross

[57] ABSTRACT

A welder's helmet has a window with an upper section of invariable light-attenuation characteristics and a dimmable lower section comprising an ultraviolet filter, an infrared filter, and an electro-optical shutter such as a liquid crystal sandwiched between a polarizer and an analyzer. A control circuit including a UV-sensitive photocell, upon sensing a welding arc or flame, operates the shutter to reduce the amount of light transmitted through the lower section of the window.

9 Claims, 8 Drawing Figures

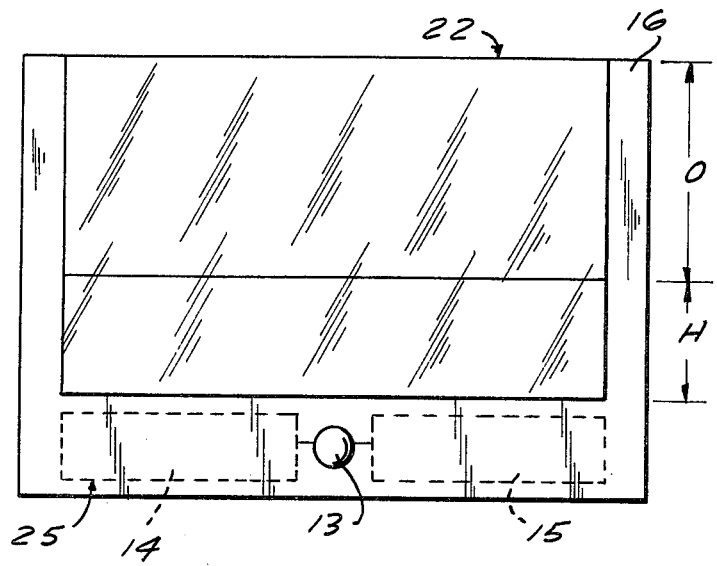
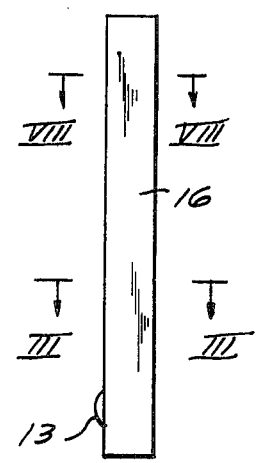
FIG. 1    FIG. 2
FIG. 3
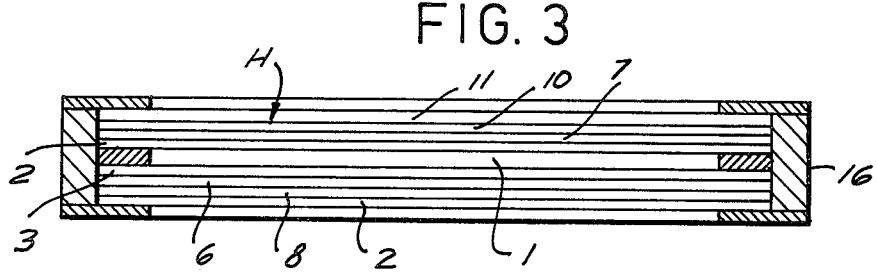
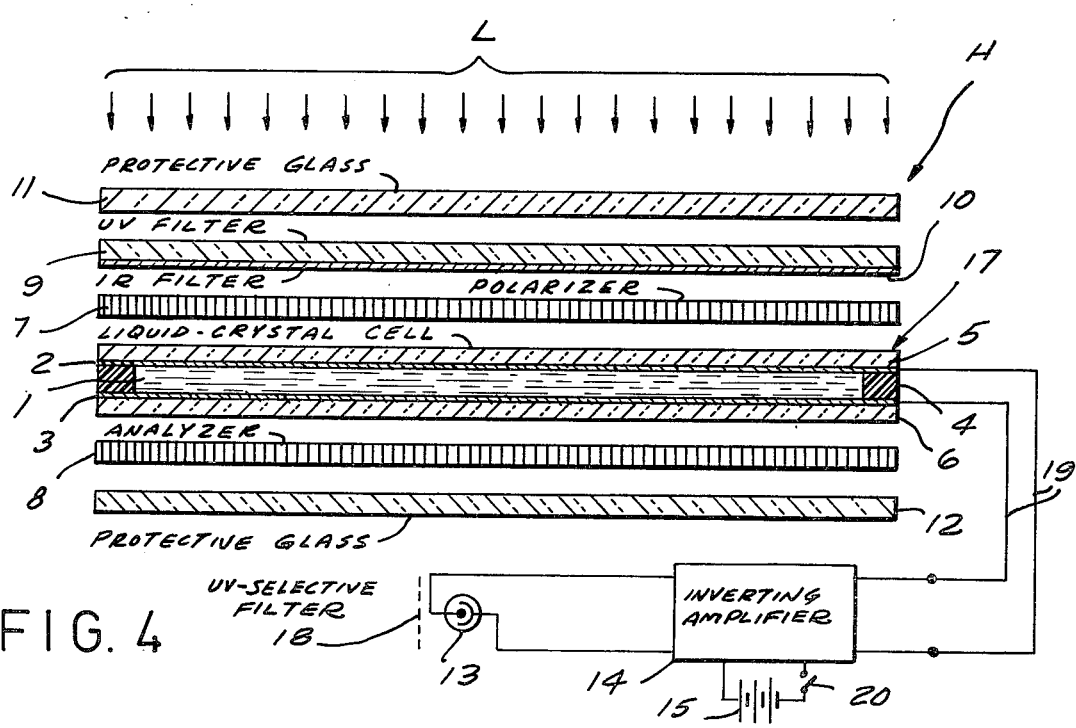
FIG. 4

FIG. 7
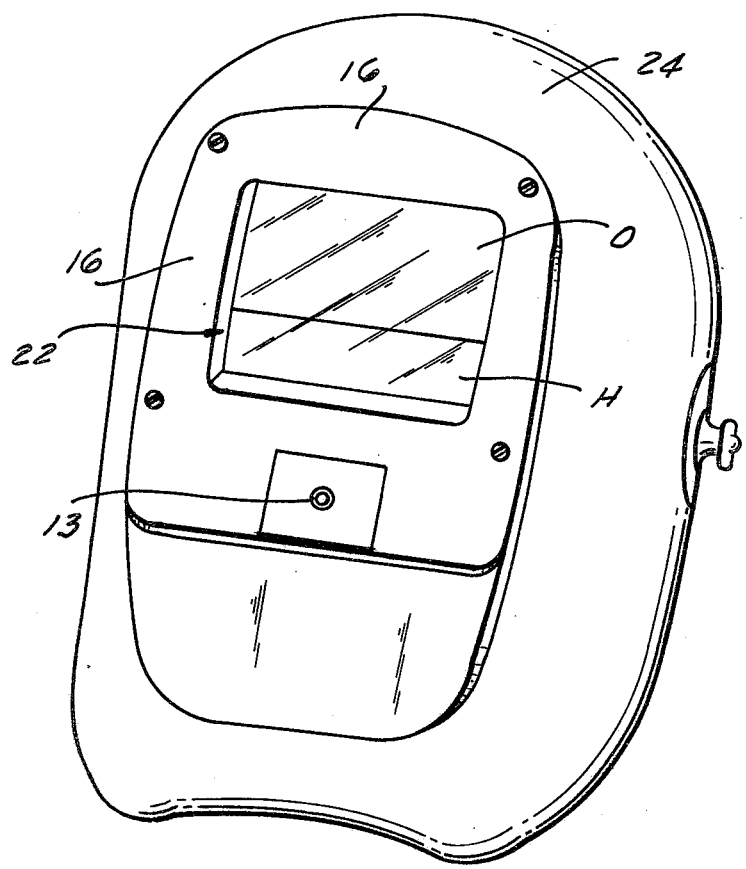
BROAD-SPECTRUM
LIGHT ATTENUATOR
BLOCKING UV
AND IR RAYS
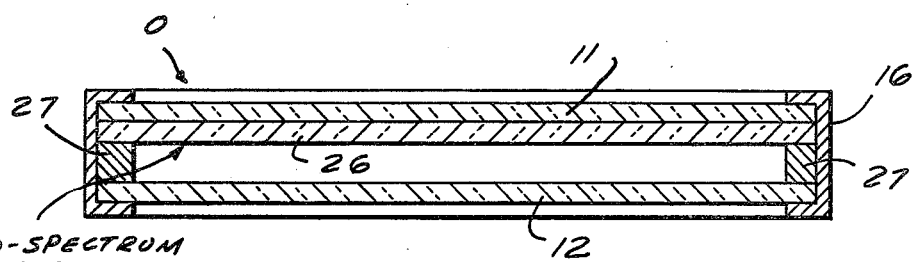
FIG. 8

LIGHT SHIELD FOR WELDER'S MASK

CROSS-REFERENCE TO RELATED APPLICATION

This is a continuation-in-part of my copending application Ser. No. 637,000 filed Dec. 2, 1975 now U.S. Pat. No. 4,071,912.

FIELD OF THE INVENTION

My present invention relates to a light shield for protecting the eyes of a welder against the glare of a welding arc or flame.

BACKGROUND OF THE INVENTION

Gas and electric-arc welding produces an extremely bright light that is rich in ultraviolet and infrared rays. Frequent or prolonged exposure to such light can blind a person. For this reason welders usually wear protective helmets or goggles provided with filters designed to stop harmful rays.

The principal difficulty with such a light-filtering device is that visible light is also greatly attenuated. Thus it is customary for the welder to strike the arc or ignite the gas flame with the goggles or helmet tilted up so that he can see what he is doing, and to put this protective gear in place only when the light generated by the welding operation is sufficient to allow him to view the workpiece. This short but frequent exposure to the unfiltered light from the arc or flame is in the long run very harmful.

It has already been proposed (see, for example, U.S. Pat. No. 3,245,315) to use an electro-optical shutter in a pair of spectacles designed to protect the eyes of the user against excessively brilliant flashes of light. A similar shutter or variable-density filter, utilizing the birefringence of a ferro-electric ceramic plate, is described in U.S. Pat. No. 3,737,211. More recently, so-called liquid crystals have been envisaged for the same purpose; see U.S. Pat. No. 3,873,804.

A shutter using a birefringent plate or a nematic-phase liquid as its electro-optical switching element generally comprises a polarizer and an analyzer between which that element is sandwiched. Thus, if the analyzer and the polarizer are relatively oriented in such a manner that incident unpolarized light is able to pass through the stack with only moderate attenuation, the application of a switching voltage to the electro-optical element under the control of a photocell responsive to a bright flash may reduce the light transmissivity of the shutter assembly to almost zero.

As disclosed in my copending application and patent identified above, such a shutter (when used as an eyeshield for a welder's headpiece) can be placed in its condition of maximum attenuation by a switchover to either an energized or a de-energized state of its electro-optical element. Although with certain liquid crystals the transition from high to low light transmissivity may take slightly longer when achieved by the removal of voltage rather than by the generation of an electric field, dimming through de-energization has the advantage that the eyes of a welder will not be suddenly exposed to the glare of an arc in the event of a failing current supply.

As described in the above-cited U.S. Pat. No. 3,873,804, a nematic-phase liquid crystal normally imparts a 90° rotation to plane-polarized light impinging with a predetermined orientation upon one of its cell walls. When an electric field of a certain minimum strength is applied across these walls, the molecules of the liquid are reoriented (from a homogeneous state paralleling the cell walls to a homeotropic state perpendicular thereto) so that such rotation will no longer occur. With crossed planes of polarization of the polarizer and the analyzer respectively adjoining these cell walls, the light transmissivity of the energized shutter drops to a small fraction of its previous value.

Light traversing a liquid crystal in the homogeneous state of its nematic-phase liquid experiences considerable scattering so that the crystal appears cloudy. Thus, the user looking through such a shutter in its high-transmissivity or "open" condition does not have a very clear view of a workpiece to be welded, for example. When the shutter is dimmed by a switchover to the homeotropic state, according to conventional practice, the scattering effect is greatly diminished so that a welder will be able to see the flame-illuminated workpiece even through the darkened cell assembly.

With a reverse arrangement, i.e. with the polarizer and the analyzer effective in parallel planes of polarization so that light transmission will be a maximum in the presence of an electric field, the cloudiness in the "open" state of the shutter disappears but the light-scattering effect in its "closed" state further reduces the visibility of the workpiece during the welding operation to an extent making it difficult for the operator to see what he is doing.

OBJECT OF THE INVENTION

The object of my present invention, therefore, is to provide an improved welder's eyeshield which gives a clear view of the work both before and after the striking of an arc while affording the necessary protection against bright light.

SUMMARY OF THE INVENTION

I realize this object, in accordance with the present invention, by providing a welder's headpiece with a compound light-filtering device which comprises a passive section of constant light attenuation in juxtaposition with a photoelectrically controlled active section of variable light transmissivity. The two sections are mounted in a frame which is so attached to the headpiece (i.e. a helmet or a pair of goggles) that the window defined by this frame is aligned with the eyes of the wearer. I prefer to mount the passive window section above the active section and to make it greater in height than the latter so that the wearer will have a broad field of view during the welding operation. Since this passive window section has no significant cloudiness, the active section can now be so designed as to be transparent to visible rays in the absence of an output signal from an associated photoelectric sensing means and to have its light transmissivity significantly reduced by the presence of such an output signal even if this darkening is accompanied by an intensified light-scattering effect as discussed above.

Advantageously the passive window section constitutes a broad-spectrum filter suppressing both infrared and ultraviolet rays in addition to visible radiation. The optical density of the passive section preferably is substantially equal to that of the active section in its de-energized low-transmissivity state.

BRIEF DESCRIPTION OF THE DRAWING

The above and other features of my invention will now be described in detail with reference to the accompanying drawing in which:

FIG. 1 is a front view of a light-filtering device embodying my invention;

FIG. 2 is a side view of the device shown in FIG. 1;

FIG. 3 is a sectional view of a shutter section, taken on the line III—III of FIG. 2;

FIG. 4 is an exploded view of the shutter section shown in FIG. 3;

FIG. 7 is a perspective view of the device of FIGS. 1-4 attached to a welder's helmet; and FIG. 8 is a cross-sectional view taken on the line VIII—VIII of FIG. 2.

SPECIFIC DESCRIPTION

Figure 5:
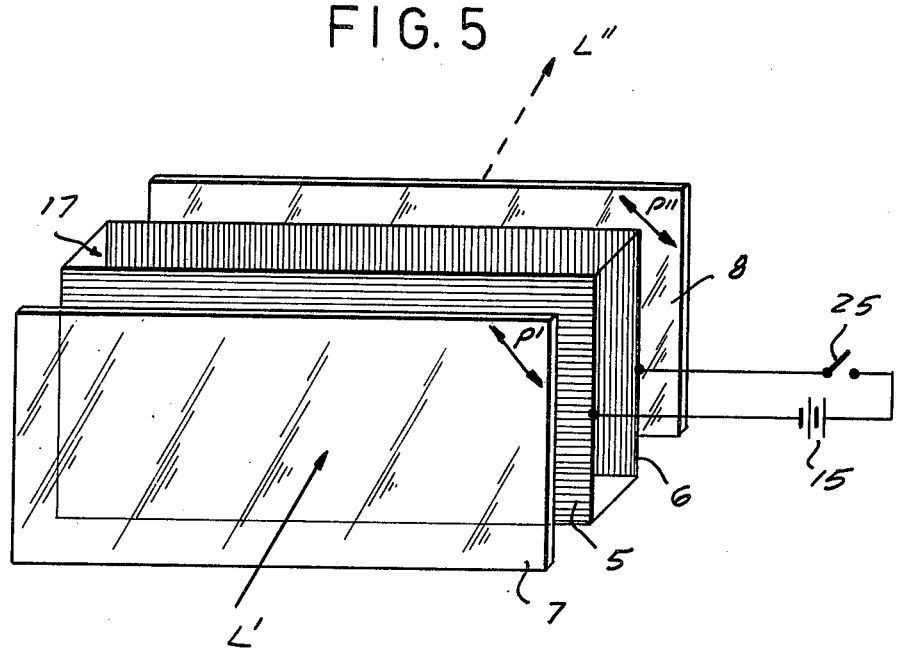
FIGS. 5 and 6 are perspective exploded views illustrating the mode of operation of the shutter section shown in FIGS. 3 and 4.

A light-filtering device according to my invention comprises, as indicated in FIG. 1, a window 22 mounted in a headpiece frame 16. Window 22 is divided into an active lower section H and a passive upper section O, the latter being shown in FIG. 8 as comprising a filter 26 strongly attenuating a broad spectrum of radiation including infrared and ultraviolet light. Also mounted in frame 16 are an amplifier 14, a photocell 13 and a battery 15 forming part of a control circuit shown in FIG. 4. Window 22 and frame 16, illustrated only schematically in FIG. 1, are shown attached to a welder's helmet 24 in FIG. 7.

Window section H, constituting an electro-optical shutter, is illustrated in greater detail in FIG. 4. Stacked in the direction of light transmission (indicated by vertical arrows L) between an outer protective plate 11 and an inner protective plate 12 of glass or transparent plastic (e.g. Plexiglas) are an ultraviolet filter 9 coated with a layer 10 acting as an infrared filter, a polarizer 7, an electro-optical switching element 17, and an analyzer 8. Element 17 comprises an outer glass plate 5 and an inner glass plate 6 provided with transparent electrically conductive electrode layers 2 and 3, respectively. Electrodes 2 and 3 are held apart a distance of 10 to 30 microns by means of spacers 4 between which a liquid crystal 1 of nematic type is sealed.

Photocell 13 is shown disposed behind a filter 18 which screens out most visible light and allows only rays characteristic of a welding operation, especially those in the ultraviolet range, to pass through. The photocell works into amplifier 14, driven by battery 15 through an on-off switch 20, which is of the inverting type so that its output leads 19, connected across electrodes 2 and 3, carry voltage when little or no light falls upon the photocell. Under these conditions the liquid-crystal cell 17 allows light from polarizer 7 to traverse the analyzer 8 so that an operator looking through window section H has a clear view of a workpiece to be welded.

When the welding arc or flame is ignited, the bright flash of light penetrating the ultraviolet-selective filter 18 renders the photocell 13 conductive and generates an output signal which cuts off the inverting amplifier 14, thus producing a zero or near-zero voltage difference across leads 19 whereby the cell 17 is switched to its alternate condition in which the passage of light through the stack of FIG. 4 is nearly cut off. Since, however, the workpiece at this instant is brightly illuminated by the welding arc or flame, the user can observe it through window section O if the view through section H is too indistinct.

FIG. 5 shows the shutter assembly 7, 8, 17 in its deenergized state, as symbolized by an open switch 25 (representative of photocell 13 and amplifier 14) in series with battery 15, in which light L′ incident upon polarizer 7 is greatly attenuated when emerging from analyzer 8 as indicated by a broken line L″. The planes of polarization of plates 7 and 8 are parallel, as denoted by arrows P′ and P″; cell walls 5 and 6 are so pretreated—as described in U.S. Pat. No. 3,873,804—that the molecules of the nematic liquid in their homogeneous state are oriented in one direction, here horizontally, in the vicinity of wall 5 and are oriented in another direction at right angles thereto, here vertically, next to wall 6. Thus, the plane-polarized light passed by plate 7 undergoes a 90° rotation on its traverse of liquid-crystal cell 17 from which it emerges with its plane of polarization perpendicular to that of plate 8. This 90° rotation is accompanied by a marked scattering effect so that the residual light L″ gives a blurred picture of the brightly illuminated workpiece.

Figure 6:
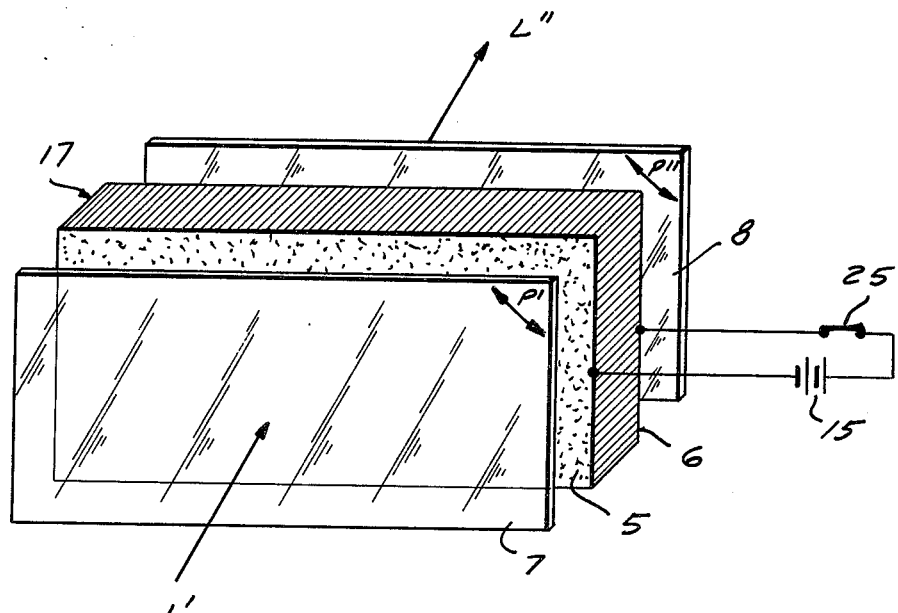

As shown in FIG. 6, closure of switch 25—i.e. the application of a d-c voltage of about 1 to 6 volts across the electrodes 2 and 3 of cell walls 5 and 6 in the nonconductive condition of photocell 13, FIG. 4—reorients the liquid-crystal molecules in a direction generally perpendicular to the cell walls so that the 90° rotation normally introduced by the cell 17 disappears. Light polarized by plate 7 in plane P′ now emerges with the same orientation from the liquid-crystal cell and easily passes the plate 8 as indicated by a solid line L″. Under these conditions, furthermore, the light-scattering effect of the nematic liquid is minimal.

In FIG. 8 I have shown the passive window section O as comprising, within frame 16, a filter plate 26 of dark mineralic glass, e.g. according to ANSI standard 787.1 (1968) with a shadow number 10. Plate 26 is bracketed by the protective plates 11 and 12 and is held separated from the latter by spacers 27. Since this plate does not significantly scatter the penetrating light rays, the user has a dimmed but unblurred view of the workpiece illuminated by the welding flame.

It will thus be seen that I have provided an improved eyeshield which gives a clear view under both ordinary and excessive illumination and is safe to the eyesight even in the event of a failure of the power supply while taking advantage of the quick switchability and low driving voltage of nematic liquids. The disclosed principles, however, are also applicable to other types of electro-optical shutters which in their "closed" state would unduly obscure an object to be observed.

I claim:

1. A welder's eyeshield comprising: a headpiece provided with a window subdivided into a passive first section of constant light attenuation and a voltage-controlled second section of variable light transmissivity juxtaposed with said first section;

photoelectric sensing means on said headpiece generating an output signal in response to incident radiation potentially damaging to the user's eyesight; and circuit means connecting said sensing means to said second section for maintaining same more highly transparent to visible rays than said first section in the absence of said output signal and for significantly reducing the light transmissivity of said second section in the presence of said output signal.

2. A welder's eyeshield as defined in claim 1 wherein said first section is located above said second section.

3. A welder's eyeshield as defined in claim 2 wherein said first section is of greater height than said second section, said sections being substantially coextensive horizontally.

4. A welder's eyeshield as defined in claim 1 wherein said second section comprises a stack of substantially coextensive layers including an ultraviolet filter, an infrared filter, a polarizer, an analyzer, and an electro-optical element between said polarizer and said analyzer, said electro-optical element being switchable by said circuit means for changing the orientation of the plane of polarization of light passing from said polarizer toward said analyzer.

5. A welder's eyeshield as defined in claim 4 wherein said electro-optical element includes a liquid crystal of nematic type having a light-scattering effect in its de-energized state but passing plane-polarized light substantially unchanged in its energized state, said polarizer and analyzer having substantially parallel planes of polarization for giving a clear view of a workpiece in said energized state.

6. A welder's eyeshield as defined in claim 6 wherein said first section comprises an ultraviolet filter and an infrared filter.

7. A welder's eyeshield as defined in claim 7 wherein the optical density of said first section substantially equals that of said second section in the de-energized state of said liquid crystal.

8. A welder's eyeshield as defined in claim 1 wherein said sensing means comprises a photosensor selectively responsive to light rays outside the visible part of the spectrum.

9. A welder's eyeshield as defined in claim 8 wherein said photosensor includes a filter selectively passing ultraviolet light.

* * * * *